(12) United States Patent
Lin et al.

(10) Patent No.: US 7,790,943 B2
(45) Date of Patent: Sep. 7, 2010

(54) INTEGRATED PROCESS FOR REMOVING BENZENE FROM GASOLINE AND PRODUCING CYCLOHEXANE

(75) Inventors: Tzong-Bin Lin, Chiayi (TW); Jyh-Haur Hwang, Dai (TW); Hung-Chung Shen, Chiayi (TW); Kuang-Yeu Wu, Plano, TX (US)

(73) Assignees: AMT International, Inc., Plano, TX (US); CPC Corporation, Taiwan, Taipei (TW)

( * ) Notice: Subject to any disclaimer, the term of this patent is extended or adjusted under 35 U.S.C. 154(b) by 1107 days.

(21) Appl. No.: 11/475,304

(22) Filed: Jun. 27, 2006

(65) Prior Publication Data

US 2007/0299294 A1    Dec. 27, 2007

(51) Int. Cl.
*C07C 7/10* (2006.01)
(52) U.S. Cl. .......................... 585/833; 585/857; 585/804
(58) Field of Classification Search ........................ None
See application file for complete search history.

(56) References Cited

U.S. PATENT DOCUMENTS

| | | | |
|---|---|---|---|
| 2,373,501 A | | 4/1945 | Peterson |
| 2,561,624 A | * | 7/1951 | Harrison ...................... 203/46 |
| 2,842,484 A | * | 7/1958 | Fleck .......................... 203/51 |
| 3,070,640 A | | 12/1962 | Pfeiffer |
| 3,202,723 A | | 8/1965 | Thonon |
| 3,293,315 A | | 12/1966 | Nixon |
| 3,434,936 A | | 3/1969 | Luther |
| 3,527,823 A | | 9/1970 | Jones |
| 3,751,504 A | | 8/1973 | Keown |
| 3,767,568 A | | 10/1973 | Chen |
| 3,796,764 A | | 3/1974 | Suggitt |
| 4,053,369 A | | 10/1977 | Cines |
| 4,140,622 A | | 2/1979 | Herout |
| 4,209,383 A | | 6/1980 | Herout |
| 4,459,426 A | | 7/1984 | Inwood |
| 4,731,496 A | | 3/1988 | Hu |
| 4,746,762 A | | 5/1988 | Avidan |
| 4,827,069 A | | 5/1989 | Kushnerick |
| 4,849,569 A | | 7/1989 | Smith, Jr. |
| 4,950,387 A | | 8/1990 | Harandi |
| 4,950,823 A | | 8/1990 | Harandi |

(Continued)

FOREIGN PATENT DOCUMENTS

JP        04041441 A      2/1992

OTHER PUBLICATIONS

E.E. Partin, Alkylation of FCC off Gas Olefins with Aromatics via Catalytic Distillation, presented at the National Petroleum Assn. meeting 1988, pp. 1-7.

*Primary Examiner*—Tam M Nguyen
(74) *Attorney, Agent, or Firm*—Cascio Schmoyer & Zervas

(57) ABSTRACT

An integrated, continuous process for transforming feedstock, e.g., reformate, which contains high levels of benzene into a low-benzene content feedstock that is suitable for gasoline blending initially removes benzene from the reformate by extractive distillation, then partially hydrogenating the high purity benzene into cyclohexane under mild conditions in a one-stage hydrogenation reactor, and thereafter recovering a cyclohexane product with high purity from the hydrogenation reactor effluent in a back-end purification step using extractive distillation. The initial or front-end separation step yields a low-benzene content reformate.

62 Claims, 2 Drawing Sheets

U.S. PATENT DOCUMENTS

| | | |
|---|---|---|
| 4,975,179 A | 12/1990 | Harandi |
| 4,992,607 A | 2/1991 | Harandi |
| 4,997,543 A | 3/1991 | Harandi |
| 5,120,890 A | 6/1992 | Sachtler et al. |
| 5,185,486 A | 2/1993 | Collin |
| 5,189,233 A | 2/1993 | Larkin |
| 5,210,333 A | 5/1993 | Bellows |
| 5,294,334 A | 3/1994 | Kaul |
| 5,399,244 A * | 3/1995 | Gentry et al. .......... 203/23 |
| 5,458,741 A | 10/1995 | Berg |
| 5,491,270 A | 2/1996 | Chin |
| 5,773,670 A | 6/1998 | Gildert |
| 5,830,345 A | 11/1998 | Lee |
| 5,856,602 A | 1/1999 | Gildert |
| 6,124,514 A | 9/2000 | Emmrich et al. |
| 6,187,980 B1 | 2/2001 | Gildert |

\* cited by examiner

INTEGRATED PROCESS FOR REMOVING BENZENE FROM GASOLINE AND PRODUCING CYCLOHEXANE

FIELD OF THE INVENTION

The present invention is directed to a process for removing benzene from a gasoline blending stock and generating cyclohexane from the benzene and, more particularly, to an integrated process that yields a reformate containing relatively low levels of benzene and a high purity cyclohexane product. The process employs extractive distillation to recover benzene from the gasoline blending stock, and hydrogenation to partially convert the benzene into cyclohexane, and extractive distillation to purify the cyclohexane.

BACKGROUND OF THE INVENTION

The United States Environmental Protection Agency (EPA) pursuant to the Clean Air Act requires gasoline to contain less than 1.0% benzene by volume beginning in the 1990's; this standard has been adopted by many countries throughout the world. To comply with this regulation, refineries have implemented various techniques to reduce the levels of benzene in gasoline, which otherwise contains approximately 2 to 3% benzene.

Gasoline is a well known fuel, generally composed of a mixture of numerous hydrocarbons including aromatics, olefins, naphthenes and paraffins having different boiling points at atmospheric pressure. The primary sources of the benzene in gasoline are the gasoline blending stocks which include naphtha from fluid catalytic cracker (FCC) units and catalytic reformer products (reformate). While FCC naphtha is the largest single blending stock for gasoline and constitutes up to 50% of the final product, the FCC naphtha itself typically contains only about 1% benzene and is therefore not the primary contributor of benzene. In contrast, reformate normally contains more than 5% benzene and given that approximately 75% of the benzene that is present in gasoline is derived from reformate, many strategies for reducing benzene levels in gasoline have focused on removing a substantial portion of the benzene from reformate prior to blending.

The most common techniques for reducing the benzene content in gasoline blending reformate include chemical processes that convert benzene to other desirable and less objectionable components for gasoline blending and physical separation that removes at least a portion of benzene.

An early approach was alkylation of benzene to yield heavier aromatics whose presence in gasoline was more acceptable. These techniques generally consisted of alkylating benzene with light olefins. Unfortunately, many of the alkylation processes were accompanied by undesirable side reactions and all of these techniques increased the costs to gasoline production significantly. Alkylation techniques are described, for example, in U.S. Pat. No. 3,293,315 to Nixon, U.S. Pat. No. 3,527,823 to Jones U.S. Pat. Nos. 4,140,622 and 4,209,383 both to Herout et al., and U.S. Pat. No. 4,849,569 to Smith.

Another feasible approach of reducing the levels of benzene in reformate was to convert benzene into cyclohexane. For examples, U.S. Pat. No. 5,773,670 to Gildert et al. discloses a process for the hydrogenation of aromatics in a petroleum stream, but the process is not selective only to benzene and therefore yields a number of undesired by-products. U.S. Pat. No. 6,187,980 to Gildert et al. discloses a process for hydrogenation of benzene to cyclohexane in a distillation column reactor where the feedstock is essentially pure benzene. U.S. Pat. No. 5,856,602 to Gildert et al. describes the hydrogenation of aromatics in a hydrocarbon stream in a distillation column reactor whereby the placement of the catalyst bed and operation of the distillation column determine which aromatics are retained in the catalyst bed for hydrogenation. U.S. Pat. No. 5,294,334 to Kaul et al. and U.S. Pat. No. 5,210,333 to Bellows et al. each disclose processes which selectively adsorb benzene from a gasoline stream and thereafter hydrogenate the benzene into cyclohexane without the need for added desorbents. A serious drawback of these approaches is that since the cyclohexane remains in the gasoline stream, there is a significant reduction in the grade of the gasoline because the octane rating of cyclohexane is much lower than that of benzene.

In order to partially recover the lost octane number, U.S. Pat. No. 5,830,345 to Lee et al. discloses a process for producing a benzene-reduced gasoline blending stock which uses a dual functional catalyst to hydrogenate benzene into cyclohexane and isomerize the cyclohexane into methylcyclopentane, which has an octane rating that is between that of cyclohexane and benzene. Again, this hydrogenation method (even with isomerization) adds to the refining costs and reduces the grade the gasoline blending stock.

Cyclohexane is commercially produced in huge quantities mainly through the hydrogenation of benzene with hydrogen gas in a fixed bed of nickel catalyst or a noble metal catalyst. Hydrogenation of aromatics is well known. For example, U.S. Pat. No. 2,373,501 to Peterson describes a liquid phase process for hydrogenating benzene to cyclohexane. U.S. Pat. No. 5,189,233 to Larkin et al. discloses a liquid phase process for benzene hydrogenation to cyclohexane whereby the liquid phase with the benzene is exposed to progressively more active catalysts. The process is said to be more selective to benzene and to provide higher yields. High pressures are employed to maintain the reactants in the liquid state.

U.S. Pat. No. 4,731,496 to Hu et al. discloses a gas phase process for hydrogenation of benzene to cyclohexane over a nickel catalyst supported on titanium oxide/zirconium oxide. In practice, benzene is contacted with hydrogen in the presence of the catalyst in a hydrogenation reactor operating at elevated temperatures and pressures. Good conversion of benzene to cyclohexane is achieved, although side reactions, such as cracking and isomerization, may occur. The cyclohexane product should have at least 99.9 wt % purity with less than 1,000 ppm of total impurities. The impurities include unconverted benzene, methyl cyclopentane (from isomerization), methyl cyclohexane (from the toluene impurity in benzene), and trace amounts of n-hexane, n-pentane, etc. (from cracking). Lowering the reaction temperature will minimize the production of by-products but at the expensive of added complexity and costs. For instance, a process that employs multi-stage reactors with inter-stage cooling to remove the heat from the highly exothermic hydrogenation reaction and higher recycling of unconverted benzene and cyclohexane product can achieve better benzene conversion. In particularly, for a four-stage reactor system, it was found that approximately 95% of the initial benzene was converted to cyclohexane in the first reaction vessel, while only 3.5%, 1%, and 0.3% of the initial benzene were converted to cyclohexane in the last three reaction vessels, respectively. Despite the better cyclohexane yield, the process is not economically attractive in view of the attendant complicated reactor system.

Examples of commercial operations that convert the benzene completely and yield high purity cyclohexane product include hydrogenation processes developed by UOP, BP and IFP. UOP's Hydrar process uses fixed platinum-based catalyst beds in a series of two or three reactors. The reaction temperatures are stepped up between 200 to 300° C. and the reactors operate at below 30 atm hydrogen partial pressure in order to achieve complete conversion per pass. To control the reactor temperature, a portion of the liquid product is recycled to dilute the benzene.

In the two-step BP hydrogenation process, the reaction temperature in stage one is controlled by recycling liquid and vapor from stage two and the effluent from the first stage is able to reach 95 wt % cyclohexane. Furthermore, temperature control of stage one by using both the sensible heat energy and heat of vaporization from the recycled cyclohexane affords good energy recovery with the added benefit that the recirculation rate of cyclohexane is within manageable limits. However, the advantages associated with the reduction in hydrogenation partial pressure and in temperature are offset by the fact that recycling means that a second reactor is needed complete the hydrogenation reaction.

Finally, the IFP process is carried out in liquid phase at 185° C. at a pressure of 20 to 35 atm and in the presence of nickel-based catalysts that are held in suspension by agitation with an external circuit. The cyclohexane product in the reactor effluent is in vapor phase thereby facilitating the partial removal of heat. A heat exchanger located in the external circuit removes the remaining portion of heat. Major drawbacks of this process are that the relatively large catalyst particles limit the catalyst activity and reduce the stability of the suspension. As is apparent, current commercial benzene hydrogenation processes which are designed to yield high purity cyclohexane products are overly complex.

The art is in need of a simple, economical method of removing purified benzene from feedstock such as reformate and converting the purified benzene into cyclohexane in a simplified hydrogenation reactor which is a part of an integrated process with interrelated steps.

SUMMARY OF THE INVENTION

The present invention is generally directly to a continuous process for transforming feedstock, e.g., reformate, which contains high levels of benzene into a low-benzene content feedstock that is suitable for gasoline blending. This is accomplished with an integrated approach whereby benzene is initially removed from the reformate by extractive distillation, the high purity benzene is then partially hydrogenated into cyclohexane under mild conditions in a one-stage hydrogenation reactor, and thereafter a cyclohexane product is recovered from the hydrogenation reactor effluent in a purification step using extractive distillation. The initial or front-end separation step yields the desired low-benzene content reformate. The process is quite flexible in that the concentration of cyclohexane in the final product can be readily adjusted, in part, by regulating the conversion rate of benzene in the hydrogenation reactor. It is expected that the concentration of cyclohexane that is produced at the back-end can range from 1% to essentially 100% cyclohexane. The high purity cyclohexane is a valuable commodity.

The invention is based, in part, on the recognition that a single hydrogenation reactor operated under mild conditions can readily achieve moderate benzene conversion rates of approximately 40 to 60% per pass with minimal or no adverse side reactions and minimized liquid recycle for quenching the reactor temperature. Specifically, essentially pure cyclohexane can be attained by lowering the cyclohexane recovery per pass and recycling the desired amount of cyclohexane with benzene into the hydrogenation reactor in order to better control the reaction temperature and conversion. By limiting the benzene conversion rate, the process does not require multiple hydrogenation reactors.

It is possible to recycle cyclohexane along with the benzene feed into the benzene hydrogenation reactor without having significant contaminants trapped in between them since cyclohexane and benzene boil at temperatures that are only 0.6° C. apart. The inventive process affords a simplified, cost effective hydrogenation scheme that requires much less energy consumption than prior commercial systems. Indeed, the back-end extractive distillation column for cyclohexane purification can be operated so as to require essentially no or minimal external energy input, instead, depending on the design requirements of the process, the back-end extractive column can function solely on the energy that is carried over from the hydrogenation reactor. The process typically employs a single solvent recovery column that recovers lean solvent, from the rich solvent streams that are discharged from the front-end and back-end extractive distillation columns, for reuse in the continuous process.

DETAILED DESCRIPTION OF PREFERRED EMBODIMENTS

Figure 1:
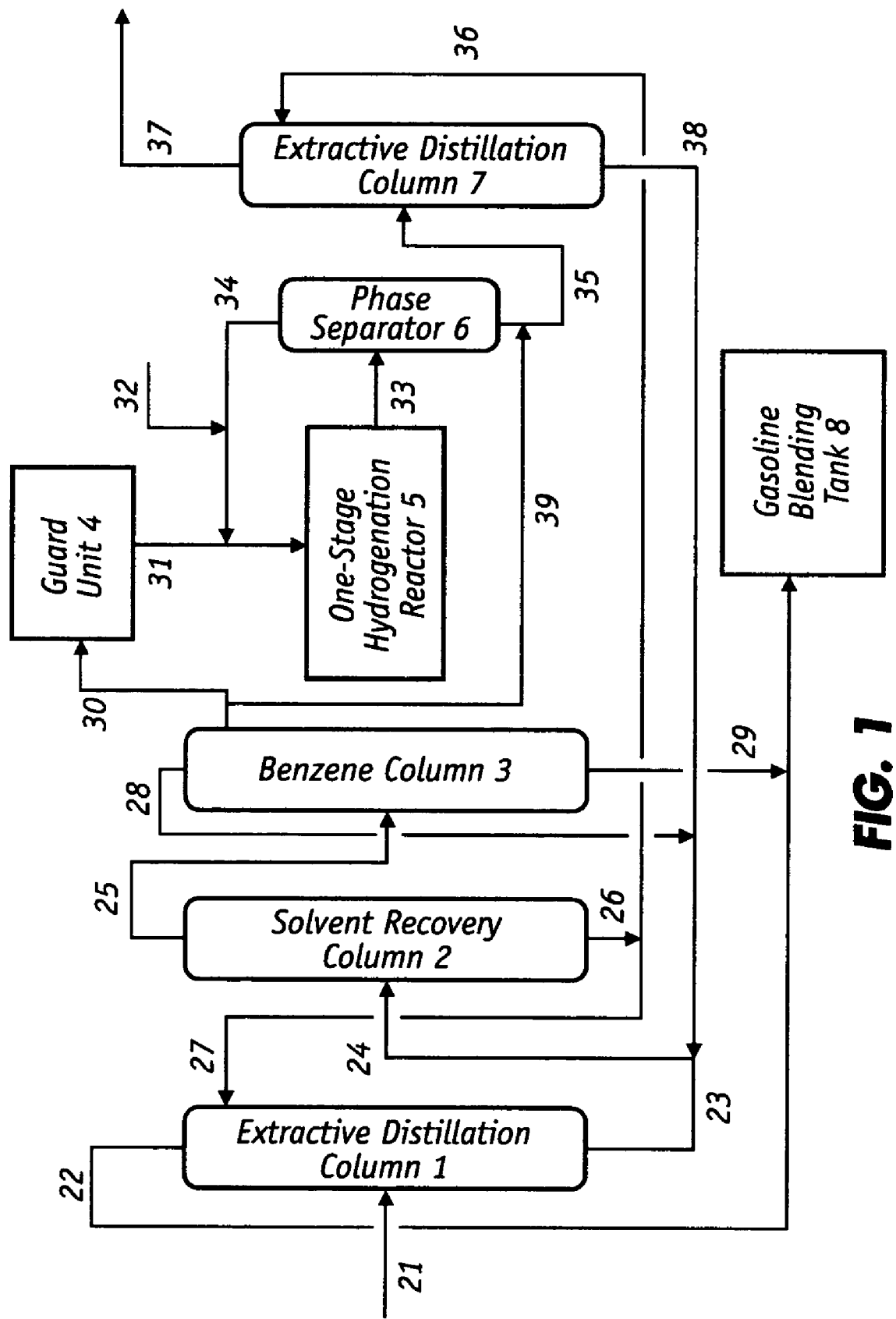
FIGS. 1 and 2 are schematic flow sheets of two alternative integrated processes for removing benzene from feedstock, partially converting the purified benzene into cyclohexane through a one-stage partial hydrogenation reactor, recovering a low-benzene feedstock that is suitable for gasoline blending and recovering a highly purified cyclohexane product.

The present invention is directed to an integrated, highly energy efficient process for removing some of the benzene from a hydrocarbon feedstock and partially hydrogenating the removed benzene to yield a high purity cyclohexane product. A feature of the invention is that the continuous process removes the benzene from the feedstock and forms cyclohexane simultaneously, that is, at the same time. The recovered low-benzene feedstock can be used as a gasoline blending stock. A preferred feedstock is reformate that contains excess benzene that needs to be removed to produce a low-benzene content reformate for gasoline blending stock. Thus, while the invention will be illustrated using reformate, it is understood that the process can accommodate other benzene-containing feedstocks.

Reformate is a complex hydrocarbon mixture containing both aromatics and non-aromatics. For use in gasoline blending, the reformate typically includes undesirable levels of benzene in a mixture of paraffins, naphthenes, toluene, xylenes, ethylbenzene, 9-carbon aromatics, 10-carbon aromatics, and other heavy hydrocarbons. While the inventive process is not limited by a specific reformate makeup, suitable feed streams typically contains 20 to 90% $C_6$ to $C_{10}$ aromatics and preferably 30 to 70% $C_6$ to $C_{10}$ aromatics. (All percentages herein are on a weight basis unless specified otherwise.) Reformate generally has at least 1% benzene and preferably 1 to 10% benzene and more preferably 3 to 6% benzene. The feed typically also contains $C_5$ to $C_{10}$ non-aromatics, in which, some of the components have boiling points that are so close to that of benzene that they cannot be separated by distillation alone.

The inventive integrated process employs three interrelated stages: (1) removal and purification of benzene from reformate, (2) partial hydrogenation of benzene in a single-stage hydrogenation reactor to produce an initial low-concentration cyclohexane product, and (3) recovery of cyclohexane to yield a high purity cyclohexane product. As will be shown, stage 3 of the integrated process uses energy that is recovered from stage 2 and therefore is executed with minimal expenditure of additional energy.

FIG. 1 illustrates one embodiment of the integrated process in which stage 1 employs an extractive distillation column 1 (EDC 1), solvent recovery column 2 (SRC 2), and benzene column 3 (BC 3), which is also referred as the azeotropic distillation column, for initially removing and purifying benzene from a reformate stream. In stage 2, a hydrogenation reactor 5 (HR 5) which is preferably a one-stage reactor partially hydrogenates the benzene into a low-concentration cyclohexane product. Finally, in stage 3, a highly purified cyclohexane product is recovered from by operation of a phase separator 6 (PS 6) and extractive distillation column 7 (EDC 7). EDC 1 can be viewed as the "front-end" extractive distillation column and EDC 7 can be viewed as the "back-end" extractive distillation column.

1. Removal and Purification of Benzene from Feedstock.

The process begins with the introduction of reformate through line 21 into the middle portion of a multi-stage EDC 1. The temperature of the reformate feed is maintained with a heat exchanger (not shown) at approximately the bubble point. Lean extractive solvent from the bottom of SRC 2 is introduced near the top of EDC 1 through line 27. In order to generate an internal reflux within EDC 1, the temperature of the lean extractive solvent is controlled with a heat exchanger (not shown) to be a few degrees lower than that of EDC 1 at the corresponding entry point. The solvent entry location is typically above the midpoint of EDC 1 and preferably it is designed to be near the top of the column such that the entry point is situated at a height that is within the upper 10 to 1% of the packed or trayed column. The flow rate of solvent stream 27 is maintained so that the solvent-to-feed (S/F) weight ratio into EDC 1 ranges from approximately 0.5:1 to 20:1 and preferably from 1:1 to 10:1.

Suitable extractive solvents include, for example, sulfolane, sulfolane with water as co-solvent, sulfolane/tetraethylene glycol mixture, sulfolane/tetraethylene glycol mixture with water as co-solvent, sulfolane/triethylene glycol mixture, and sulfolane/triethylene glycol mixture with water as co-solvent, and mixtures thereof. A preferred solvent is sulfolane with water as the co-solvent, where the water content in sulfolane typically ranges from 0.01 to 10% and preferably from 0.1 to 3%. Less preferred extractive solvents include nitrogen containing solvents, such as N-formyl morpholine, morpholine, N-methyl-2-pyrrolidone, and 2-pyrrolidone. These solvents or their nitrogen containing fragments, which are derived from thermal decomposition of the solvents, may adversely affect some of the benzene hydrogenation catalysts used in HR 5.

An overhead stream 22 which is withdrawn or collected from the top of EDC 1 includes (i) essentially all the $C_7$ and lighter non-aromatics that were present in reformate feed stream 21 and (ii) minor amounts of benzene. The overhead stream 22, which should not contain heavier aromatics or heavier non-aromatics, is condensed by a condenser (not shown). A portion of overhead stream 22 is recycled back into EDC 1 as reflux at a location that is above the solvent tray in order to quench entrained solvents in the rising vapor stream. The reflux ratio, which is the weight ratio of the overhead condensate that is returned to EDC 1 to the overhead product, typically ranges from 0.1:1 to 20:1 and preferably ranges from 0.1:1 to 5:1. The overhead product with substantially reduced benzene content is transferred to a gasoline blending tank 8 via line 22. The vapor flow within EDC 1 is generated by a bottom reboiler (not shown), which is heated by steam or hot oil at a rate that is sufficient to control the column bottom temperature and the overhead stream composition and flow rate. The reboiler temperature typically ranges from 60 to 250° C. and preferably from 80 to 200° C. The pressure within EDC 1 typically ranges from 0 to 8 atmospheres (atm) (absolute) and preferably from 0 to 5 atm (absolute).

A stream containing the major portion of benzene and essentially all the $C_{7+}$ aromatics and only $C_8$ and heavier non-aromatics from the reformate feed is withdrawn or collected from the bottom of EDC 1 through line 23. This stream 23 is combined with stream 28 (which contains benzene, cyclohexane, and water) and stream 38 (which contains benzene, cyclohexane, and solvent) and fed into the middle portion of SRC 2 via line 24.

To minimize the SRC 2 bottom temperature and completely recover hydrocarbons from the extractive solvent, SRC 2 is optionally operated under mild vacuum conditions; in addition, steam stripping is established by injecting steam at a location that is near the bottom of the column. The vacuum level of SRC 2 is typically in the range of 0 to 0.7 atm (absolute) and preferably in the range of 0.10 to 0.5 atm (absolute). The flow of hydrocarbon vapor is generated by a bottom reboiler (not shown) which is heated by steam or hot oil at a rate sufficient to control the column bottom temperature, bottom lean solvent composition, and the overhead hydrocarbon recovery. The reboiler temperature generally ranges from 50 to 250° C. and preferably from 80 to 200° C. It is preferred that the overhead stream 25 be condensed with a condenser (not shown) and a portion of the condensate recycled back into SRC 2 near the top of the column as reflux to quench the entrained solvent in the rising vapor stream. The remaining portion of the condensate overhead stream is fed into the middle portion of BC 3.

Since it is expected that essentially all non-aromatic components with boiling points that are near that of benzene will be removed from EDC 1 in overhead stream 22, a mixture that includes essentially only of benzene, cyclohexane and azeotropic amounts of water is recovered as the overhead product 28 of BC 3. The overhead of EDC 1 typically comprises 1 to 20% and preferably 5 to 10% of the benzene of the feedstock. The water content in the benzene stream from BC 3 is preferably less than 500 ppm and more preferably less than 200 ppm, in order to protect the down-stream hydrogenation catalysts, even though some benzene hydrogenation catalysts have significant water tolerance. To achieve this goal with minimal cost, BC 3 also serves as a conventional azeotropic distillation column (ADC), wherein both azeotropes of benzene/water and cyclohexane/water, which exhibit essentially the same azeotropic temperature (69.4-69.8° C.), are removed from the overhead of BC 3 and the dried mixture of benzene and cyclohexane is withdrawn from a benzene sidestream (or side-cut) of the column via line 30. The side-cut typically contains essentially only benzene and cyclohexane with 100 to 1000 and preferably 100 to 200 ppm water. All the other components in the feed to BC 3 are recovered in the bottom stream which is transferred to gasoline blending tank 8 via line 29. The azeotropes of benzene/water and cyclohexane/water from the overhead steam 28 of BC 3 are recycled to SRC 2 via line 24. BC 3 also employs an overhead reflux stream (not shown) and a bottom reboiler (not shown).

2. Partial Hydrogenation of Benzene to Cyclohexane

The mixture of benzene and cyclohexane with minimized water content is preferably pretreated to remove excess contaminants that may adversely affect hydrogenation catalysts, especially if nitrogen-containing solvents are used in EDC 1 and EDC 7. Thus, stream 30 is fed to a guard unit 4, where conventional adsorbents remove various contaminants such as sulfur, nitrogen (if any), and other polar molecules in the mixture. The adsorbents can be a composite or arranged in separate beds. The level of treatment depends on the sensitivity of the hydrogenation catalysts. The water content of the dried and desulfurized benzene feed stream 31 is typically in the range of 5 to 500 ppm and preferably 10 to 100 ppm and the sulfur content is typically in the range of 0.1 to 1000 ppm and preferably 0.5 to 10 ppm. Make-up hydrogen containing at least 90% and preferably 95% hydrogen is fed to HR 5 through line 32 as needed.

HR 5 can be any suitable reactor such as conventional one-stage fixed bed or slurry reactors loaded with hydrogenation catalysts, such as nickel or platinum, that are supported on alumina, silica or similar supports as described in U.S. Pat. No. 3,070,640 to Pfeiffer et al., which is incorporated herein by reference. Alternatively, HR 5 can be a gas phase reactor that converts benzene into cyclohexane by hydrogenation. A suitable reactor employs nickel catalyst that is supported by a mixture of titanium dioxide and zirconium dioxide as described in U.S. Pat. No. 4,731,496 to Hu, et al., which is incorporated herein by reference. The operating conditions of HR 5 including temperature, hydrogen partial pressure, and liquid hourly space velocity (LHSV) are selected to permit only partial benzene conversion which typically ranges from 5 to 95% and preferably from 40 to 60% conversion of benzene to cyclohexane per pass. This strategy effectively prevents isomerization reactions that would yield methyl cyclopentane (MCP) and cracking reactions that would yield light hydrocarbons. The average reactor temperature is typically maintained between 100 to 300° C. and preferably between 120 to 250° C. The reactor pressure is typically maintained at a level from 1 to 70 atm (absolute) and preferably from 10 to 50 atm (absolute). LHSV of the reactor is typically in the range of 1 to 15 $hr^{-1}$ and preferably in the range of 1 to 8 $hr^{-1}$. Finally, the molar ratio of benzene feed to hydrogen is typically from 1:1 to 30:1 and preferably at 4:1 to 15:1.

Since there are essentially no isomerization or cracking reactions in the hydrogenation reactor under low temperature and high LHSV operating conditions, no stripping column is required to remove MCP and light hydrocarbons from effluent 33 of HR 5, which contains essentially only excess hydrogen, unconverted benzene and cyclohexane. PS6 separates hydrogen from effluent 33 and the excess hydrogen is removed from the overhead of PS 6 and recycled back to HR 5 via line 34.

3. Purification of Cyclohexane

The degassed reactor effluent is withdrawn or collected from the bottom of PS 6 and transferred to the middle portion of EDC 7 through line 35. A feature of the process is that the temperature of stream 35, which contains cyclohexane and benzene, is approximately equal to that of the bottom temperature of HR 5. This means that stream 35 can be vaporized by pressure reduction as it is fed into EDC 7 into saturated or superheated vapor. Therefore, the energy input into EDC 7 can be substantially reduced or even essentially eliminated so that no reboiler for EDC 7 is required.

Another feature of the process is that the purity of the cyclohexane that is generated in EDC 7 and collected via overhead stream 37 can be readily controlled. In particular, it is recognized that higher cyclohexane product purity can be achieved by lowering the product recovery in EDC 7. That is, in order to assure that the process achieves the desired degree of cyclohexane purity, a certain portion of cyclohexane is allowed to pass down the column along with benzene and solvent as a recovery loss per pass. In this fashion, an overhead stream 37 containing highly purified cyclohexane with 99.9% or higher purity can be obtained. Typically, EDC 7 is operated under conditions whereby the purity of the final cyclohexane product that produced is in the range of 99 to 100% and preferably in the range of 99.5 to 99.9%. Typically, the recovery of cyclohexane can be adjusted to be in the range of 1 to 99% and preferably in the range of 50 to 95%.

In a preferred embodiment, cyclohexane from the recovery loss is a diluent in the feed for HR 5 for controlling the reactor temperature and conversion. In particular, rich solvent comprising of benzene, cyclohexane (the recovery loss in EDC 7) and solvent is withdrawn or collected from the bottom of EDC 7 and is processed through SRC 2 and then BC 3, to recover only dried benzene and cyclohexane from a side-cut of BC 3, which is used as feed to HR 5. Since all non-aromatic components having boiling points near that of benzene are removed by the overhead stream from EDC 1 and the boiling points of benzene and cyclohexane (recycled from EDC 7) are almost identical (80.1° C. vs. 80.7° C.), the side-cut stream (line 30) should contain essentially only benzene and cyclohexane.

To control the two-liquid phase region in EDC 7, a vapor mixture of benzene and cyclohexane from the side-cut of BC 3 is optionally transferred through line 39 into EDC 7 to adjust the cyclohexane and benzene composition in the feed to EDC 7. Thus, a portion of the side-cut is by-passed HR 5. The concentration of cyclohexane in the feed is maintained in the range of 10 to 90% and preferably in the range of 40 to 60% in order to control the two-liquid phase region that develops in EDC 7. Both EDC 1 and EDC 7 use the same extractive solvent and share the same solvent recovery column (SRC 2). (Alternatively, rich solvent from EDC 7 can be recovered in a separate solvent recovery column.) Lean extractive solvent from the bottom of SRC 2 is introduced to near the top of EDC 7 through line 36. Again, temperature of the lean extractive solvent is controlled with a heat exchanger (not shown) to be at a temperature that is a few degrees lower than that of the column temperature at the corresponding entry point to generate internal reflux within the column. The solvent entry location is typically above the midpoint of EDC 7 and preferably it is positioned near the top of the column such that the entry point is situated at a height that is within the upper 10 to 1% of the column. The solvent-to-feed weight ratio (S/F) to EDC 7 ranges from approximately from 0.5:1 to 20:1 and preferably from 1:1 to 10:1. A portion of the overhead stream 37 is recycled back into EDC 7 as reflux at a location above the solvent tray to quench entrained solvents in the rising vapor stream. The reflux ratio is in the range of 0.1:1 to 20:1 and preferably in the range of 0.1:1 to 5:1. The pressure within EDC 7 is maintained at 0 to 8 atm (absolute) and preferably at 0 to 5 atm (absolute). The high purity cyclohexane product is withdrawn or collected from the overhead stream 37 while rich solvent containing benzene and various amounts of cyclohexane is withdrawn from the bottom of the column via line 38. The level of cyclohexane recovery in EDC 7 is monitored by analyzing the content of line 38 and this level can be controlled by adjusting the operating parameters of EDC 7 in order to meet desired purity requirements for the overhead cyclohexane product as well as the desired cyclohexane concentration in the feed stream to HR 5.

Figure 2:
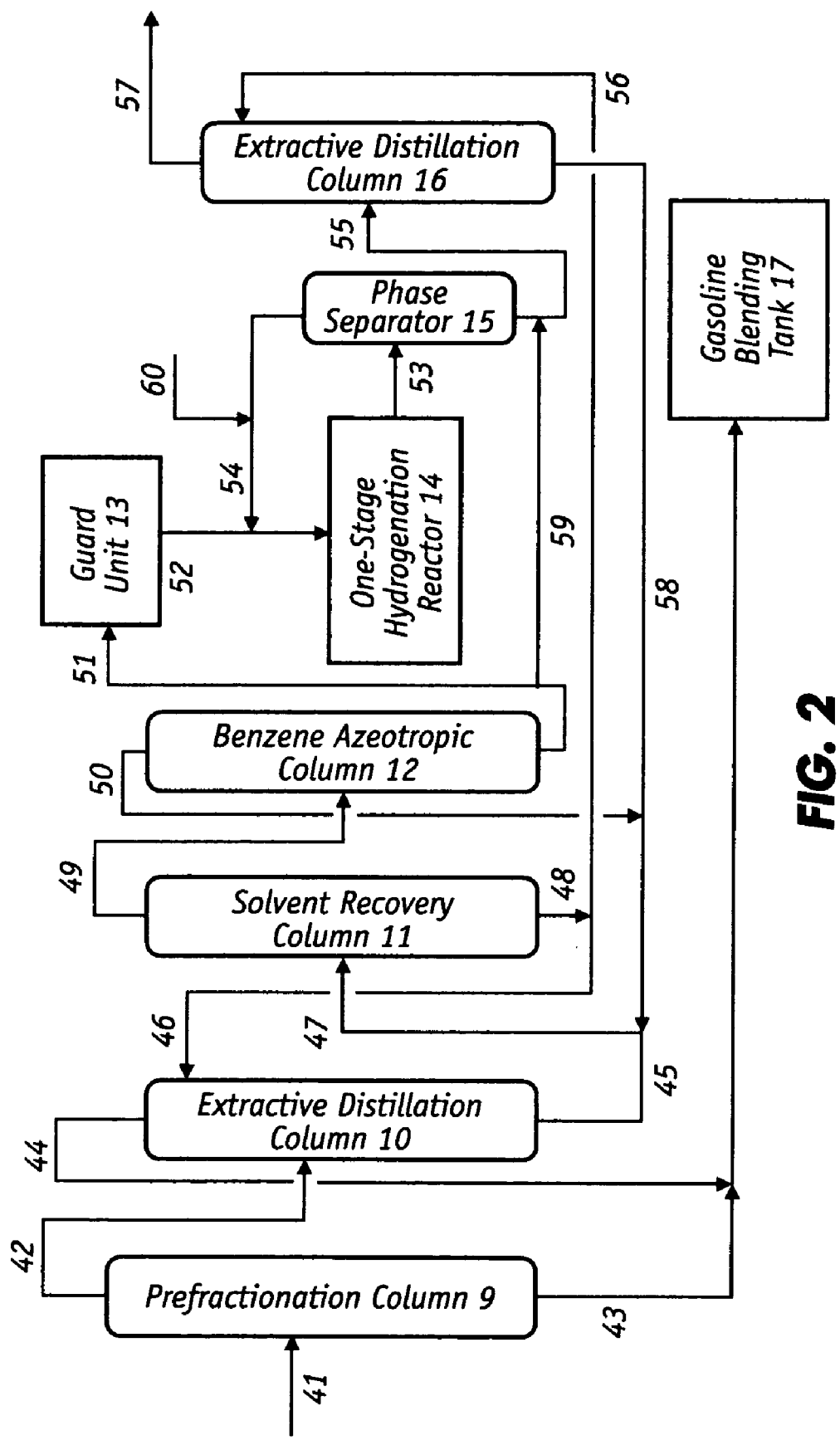

FIG. 2 illustrates another embodiment of the integrated process for removing benzene from a gasoline feedstock and partially converting the benzene into cyclohexane. The process employs three interrelated stages with stage 1 employing a prefractionation column 9 (PFC 9), an extractive distillation column 10 (EDC 10), solvent recovery column 11 (SRC 11), and benzene azeotropic column 12 (BAC 12) for initially removing and purifying benzene from the reformate stream.

In stage 2, a one-stage hydrogenation reactor 14 (HR 14) partially hydrogenates the benzene into a low-concentration cyclohexane product. Finally, a highly purified cyclohexane product is recovered from a low-concentrate cyclohexane stream by operation of a phase separator 15 (PS 15) and extractive distillation column 16 (EDC 16). The same extractive solvent(s) employed in the process illustrated in FIG. 1 can be used.

1. Removal and Purification Benzene from the Feedstock

As shown in FIG. 2, reformate is fed via line 41 into PFC 9 where $C_7$ and heavier aromatics and $C_8$ and heavier non-aromatics are removed from the bottom of the column through line 43 and stored in the gasoline blending tank 17. The overhead from PFC 9 which contains essentially only benzene and $C_7$ and lighter non-aromatics is fed into EDC 10 through line 42. The overhead from PFC 9 typically contains 20 to 90% benzene and preferably 30 to 70% benzene; it also contains $C_5$ to $C_7$ non-aromatics some of which have boiling points so close to that of benzene that they cannot be separated by distillation alone. The temperature of the reformate feed into EDC 10 is maintained with a heat exchanger (not shown) at approximately the bubble point. Lean extractive solvent from the bottom of SRC 11 is introduced near the top of EDC 10 through line 46. In order to generate internal reflux within the EDC 10, the temperature of the lean extractive solvent is controlled with a heat exchanger (not shown) to be a few degrees lower than that of the EDC 10 at the corresponding entry point. The solvent entry location is typically above the midpoint of EDC 10 and preferably near the top of the column such that the entry point is situated at a height that is within the upper 10 to 1% of the packed or trayed column. The flow rate of solvent stream 46 is maintained so that the solvent-to-feed (S/F) weight ratio into EDC 10 ranges approximately from 0.5:1 to 20:1 and preferably from 1:1 to 10:1.

An overhead stream 44, which contains essentially all the $C_7$ and lighter non-aromatics that were present in reformate feed 42 and only traces of benzene, is withdrawn from the top of EDC 10. The overhead stream 44 is preferably condensed by a condenser (not shown) prior to entering the gasoline blending tank 17 via line 44. A portion of the overhead stream is recycled back to EDC 10 as reflux at a location that is above the solvent tray to quench entrained solvents in the rising vapor stream. The reflux ratio, which is the weight ratio of the overhead condensate that is returned to EDC 10 to the overhead product, typically ranges from 0.1:1 to 20:1 and preferably ranges from 0.1:1 to 5:1. The vapor flow within EDC 10 is generated by a bottom reboiler (not shown), which is heated at a rate to that is effective to control the column bottom temperature and the overhead stream composition and flow rate. The reboiler temperature typically ranges from 50 to 200° C. and preferably from 60 to 180° C. The pressure within EDC 10 typically ranges from 0 to 8 atm (absolute) and preferably from 0 to 5 atm (absolute).

Stream 45 which contains essentially only benzene and solvent is withdrawn from the bottom of EDC 10. This stream 45 typically contains at least 80 to 100% and preferably at least 90 to 99% of the total benzene that is present in feed stream 42 that is introduced into EDC 10. Stream 45 (which contains benzene and solvent), stream 50 (which contains benzene, cyclohexane, and water), and stream 58 (which contains benzene, cyclohexane, and solvent) are combined and fed to the middle portion of SRC 11 via line 47.

To minimize the SRC 11 bottom temperature and completely recover benzene and cyclohexane from the solvent, SRC 11 is optionally operated under mild vacuum and subject to steam stripping by injecting steam at a location that is near the bottom of the column. The vacuum level of SRC 11 is typically in the range of 0 to 0.7 atm (absolute) and preferably in the range of 0.10 to 0.5 atm (absolute). The flow of hydrocarbon vapor is generated by a bottom reboiler (not shown) which is heated at a rate to effectively control the column bottom temperature, bottom lean solvent composition, and the overhead hydrocarbon recovery. The reboiler temperature generally ranges from 50 to 200° C. and preferably from 80 to 180° C.

The overhead stream 49 is condensed with a condenser (not shown) and a portion is recycled back into SRC 11 near the top as reflux to quench entrained solvents in the rising vapor stream. The remainder of the condensed overhead stream is fed via line 49 into the middle portion of BAC 12, which serves to substantially reduce the water content of stream 49 in order to protect the down-stream benzene hydrogenation catalysts. Even though some benzene hydrogenation catalysts have significant water tolerance, nevertheless, the water content in the benzene/cyclohexane feed to the HR 14 is preferably kept to a level of less than 500 ppm and more preferably of less than 200 ppm. In BAC 12, both benzene and cyclohexane form minimum-boiling azeotrope with water separately and both azeotropes boil essentially at the same temperature (69.4-69.8° C.) and are removed from the overhead and recycled back to SRC 11 via lines 50 and 47. A dried mixture of benzene and cyclohexane is withdrawn from the bottom stream 51 of BAC 12. This bottom stream can comprise essentially only benzene and cyclohexane with 100 to 1000 and preferably 100 to 200 ppm water. BAC 12 also employs an overhead reflux stream (not shown) and a bottom reboiler (not shown).

2. Partial Hydrogenation of Benzene to Cyclohexane

The bottom stream 51 from BAC 12, which contains the dried benzene and cyclohexane mixture, may be treated to remove contaminants that may be harmful to hydrogenation catalysts, especially if nitrogen-containing solvents are used in EDC 10 and EDC 16. Thus, bottom steam 51 can be directed to a guard unit 13 where conventional adsorbents remove excess water, sulfur, and nitrogen (if any) so that the water content in the feed to the one-stage hydrogenation reactor HR 14 is in the range of 5 to 500 ppm and preferably in the range of 10 to 100 ppm and the sulfur content in the feed is in the range of 0.1 to 1,000 ppm and preferably in the range of 0.5 to 10 ppm. The dried and desulfurized benzene is introduced into HR14 through line 52 while make-up hydrogen containing at least 90% and preferably 95% of hydrogen is fed to HR 14 through line 60 as needed.

Like reactor HR 5, HR 14 can be a one-stage fixed bed or slurry bed reactor that is equipped with hydrogenation catalyst, such as nickel or platinum, which is supported on alumina, silica or similar supports. Alternatively, HR 14 can be a gas phase reactor that employs suitable catalysts that catalyzes the hydrogenation of benzene into cyclohexane. For example, it can be fixed bed reactor comprising a nickel catalyst that is supported on a mixture of titanium dioxide and zirconium dioxide. The operating parameters for HR 14, including temperature, hydrogen partial pressure, liquid hourly space velocity (LHSV), and molar ratio of benzene to hydrogen are comparable to those for HR 5 in FIG. 1. In particular, the operating conditions of HR 14, such as low temperature and high LHSV, are selected to yield partial hydrogenation of benzene per pass with the concomitant effect of essentially preventing isomerization reactions that produce methyl cyclopentane (MCP) and cracking reactions that produce light hydrocarbons from occurring.

The practical absence of isomerization and cracking means that the effluent stream 53 from HR 14 contains essentially only excess hydrogen, unconverted benzene and cyclohexane. As is apparent, no stripping column is needed to remove MCP and the light hydrocarbons since these components are not generated. PS 15 separates hydrogen from effluent 53 and excess hydrogen is removed from the overhead of PS 15 and recycled back to HR 14 via line 54.

3. Purification of Cyclohexane

The third stage of this alternate process is analogous to that illustrated in FIG. 1. In particular, degassed reactor effluent from the bottom of PS 15 is transferred to the middle portion of EDC 16 through line 55. Again, stream 55 can be fed into EDC 16 in the form of saturated or super-heated vapor which minimizes or even eliminates the energy input into EDC 16, i.e., no reboiler is required. As in the case of EDC 7 in FIG. 1, by lowering the cyclohexane recovery in EDC 16 very high purity cyclohexane with 99.9% or higher purity in the column overhead can be produced and withdrawn through line 57. This procedure affords a very easy and flexible technique of assuring the quality of the cyclohexane produced. By operating EDC 16 to allow a certain portion of cyclohexane to go down the column along with benzene and the solvent as a recovery loss per pass, the purity of cyclohexane can be controlled to be in the range of 99 to 100% and preferably in the range of 99.5 to 99.9%. The recovery of cyclohexane is adjusted in the range of 1 to 99% and preferably in the range of 50 to 95%. In a preferred embodiment, the cyclohexane from the recovery loss is a diluent for the feed to HR 14 to control the reactor temperature and conversion. Specifically, rich solvent which comprises benzene, cyclohexane (from the recovery loss in EDC 16) and the solvent that is withdrawn from the bottom of EDC 16 is processed through SRC 11 and BAC 12 that to recover only benzene and cyclohexane from the bottom of BAC 12, as the feed to HR 14 through line 51. Since the boiling points of benzene and cyclohexane are almost identical (80.1° C. vs. 80.7° C.), essentially no impurity will be trapped between these two components in line 51.

To control the two-liquid phase region in EDC 16, a mixture containing benzene and cyclohexane from the bottom of BAC 12 is optionally transferred through line 59 to adjust the cyclohexane and benzene composition in the feed to EDC 16. The cyclohexane concentration in the feed to EDC 16 is maintained in the range of 10 to 90% and preferably in the range of 40 to 60 wt % in order to control the two-liquid phase region that develops in EDC 16. Both EDC 10 and EDC 16 use the same extractive solvent and share the same solvent recovery column (SRC 11). (Alternatively, rich solvent from EDC 16 can be recovered in a separate solvent recovery column.) Lean extractive solvent from the bottom of SRC 11 is introduced to near the top of EDC 16 through line 56. The temperature of the lean extractive solvent is controlled with a heat exchanger (not shown) to a temperature that is a few degrees lower than the column temperature at the corresponding entry point to generate internal reflux within the column. The solvent entry location on the column can be in the same vertical height range as that of EDC 7 in FIG. 1. In addition, the solvent-to-feed weight ratio, reflux ratio, operating temperature and pressure of EDC 16 are regulated to be in the ranges similar to those of EDC 7. Cyclohexane product with 99 to 100% and typically 99.5 to 99.9% purity can be achieved and withdrawn from the overhead stream 57, while rich solvent containing benzene and varying amounts of cyclohexane is withdrawn from the bottom of the column via line 58. The level of cyclohexane recovery in EDC 16 is adjusted to accommodate the purity requirement for the overhead cyclohexane product as well as the desired cyclohexane concentration in the feed stream to HR 14.

EXAMPLES

The following examples are presented to further illustrate the preferred embodiments and the novel features of the present invention and are not intended to limit the scope of the invention. Data in Examples 1-3 were derived by computer simulation whereas data in Examples 4-6 were derived from pilot plant operations.

Example 1

Referring to FIG. 1, 100 Kg/Hr of reformate feed is fed to tray 15 and 350 Kg/Hr of lean solvent containing 99.2% sulfolane and 0.8% water is fed to tray 4 of Extractive Distillation Column 1, which contains 25 theoretical trays. The solvent-to-feed water ratio (S/F) is approximately 3.5. Table 1 sets forth the composition of the reformate feed.

TABLE 1

| Component | Weight % | Component | Weight % |
|---|---|---|---|
| $C_{5-}$ | 4.01 | $C_6$ | 9.61 |
| Benzene | 5.43 | 2,2 Dimentyl Pentane | 2.21 |
| 2,3 Dimethyl Pentane | 2.77 | n-Heptane | 1.41 |
| $C_7$ Olefins | 0.49 | $C_7$ Naphthenes | 0.29 |
| Toluene | 15.60 | $C_8$ Paraffins | 1.26 |
| $C_8$ Naphthenes | 0.32 | n-Octane | 0.20 |
| Ethylbenzene | 3.85 | Xylenes | 18.01 |
| $C_{9+}$ Naphthenes | 0.06 | $C_{9+}$ Paraffins | 1.08 |
| $C_{9+}$ Aromatics | 33.42 | | |

EDC 1 is operated at a temperature of 156° C. in the bottom and 57° C. in the top, under a pressure of 1.6 atm in the bottom and 1.1 atm in the top, to remove 23 Kg/Hr of overhead stream containing all $C_7$ and lighter non-aromatic components for gasoline blending after decanting the water from the stream. Nearly 100% of the benzene in the reformate feed that is extracted by the solvent goes to the bottom along with other heavier components as the rich solvent.

Approximately, 427 Kg/Hr of rich solvent is withdrawn from the bottom of EDC 1 and fed to tray 11 of SRC 2, which contains 22 theoretical trays. All the hydrocarbons are stripped from the solvent in SRC 2 under 0.7 atm pressure (vacuum) in the top, with 70 Kg/Hr stripping steam fed to the bottom (tray 22) of SRC 2. The bottom temperature of SRC 2 is 159° C. The stream of 147 Kg/Hr is withdrawn from the top of SRC 2 and is decanted to remove 69 Kg/Hr water. The hydrocarbon phase from the decanter has the composition shown in Table 2.

TABLE 2

| Component | Weight % | Component | Weight % |
|---|---|---|---|
| $C_{5-}$ | 0.00 | $C_6$ | 0.00 |
| Benzene | 6.97 | 2,2Dimethyl Pentane | 0.00 |
| 2,3Dimethyl Pentane | 0.00 | n-Heptane | 0.00 |
| $C_7$ Olefins | 0.00 | $C_7$ Naphthenes | 0.00 |
| Toluene | 20.03 | $C_8$ Paraffins | 0.00 |
| $C_8$ Naphthenes | 0.30 | n-Octane | 0.26 |
| Ethylbenzene | 4.95 | Xylenes | 23.12 |
| $C_{9+}$ Naphthenes | 0.08 | $C_{9+}$ Paraffins | 1.38 |
| $C_{9+}$ Aromatics | 42.91 | | |

The data in Table 2 show that all the components with boil points near that of benzene are removed by EDC 1 and toluene has the closest boiling point to benzene. Therefore, in this computer simulation, by feeding the SRC 2 overhead stream to a distillation column, pure benzene is recovered as the only overhead product and all other components are recovered from the bottom of the column for gasoline blending. This example demonstrates that the total recovery of pure benzene can be achieved by feeding the whole reformate feed (without prefractionation) to an extractive distillation unit using sulfolane/water as the solvent.

Example 2

This example illustrates another process to recover pure benzene with high recovery from the reformate feed. Referring to FIG. 2, 100 Kg/Hr of reformate with the composition shown in Table 1 is fed to tray 14 of the Prefractionation Column 9 containing 25 theoretical trays, to yield 79 Kg/hr bottom stream for gasoline blending, and 21 Kg/Hr overhead stream containing the components listed in Table 3.

TABLE 3

| Component | Weight % | Component | Weight % |
|---|---|---|---|
| $C_{5-}$ | 19.10 | $C_6$ | 45.70 |
| Benzene | 23.95 | 2,2Dimethyl Pentane | 9.98 |
| 2,3Dimethyl Pentane | 1.20 | n-Heptane | 0.02 |
| $C_7$ Olefins | 0.04 | | |

This overhead stream is then fed to tray 15 of Extractive Distillation Column 10 containing 25 theoretical trays, while the solvent containing 99.2% sulfolane and 0.8% water is fed to tray 4 of the column. The S/F is approximately 3.5. EDC 10 is operated at a temperature of 158° C. in the bottom and 52° C. in the top, under a pressure of 1.6 atm in the bottom and 1.1 atm in the top, to remove 16 Kg/Hr overhead stream consisting of all the non-aromatic components for gasoline blending after decanting the water from the stream. Benzene alone is extracted by the solvent in the column and yielded as the bottom product (the rich solvent).

Approximately, 79 Kg/Hr of rich solvent is fed to tray 11 of Solvent Recovery Column 11, which contains 22 theoretical trays. All the hydrocarbons are stripped from the solvent in SRC 11 under 0.7 atm pressure (vacuum) in the top, with 8 Kg/Hr stripping steam fed to the bottom (tray 22) of SRC 11. The bottom temperature of SRC 11 is 159° C. A stream of 12.7 Kg/Hr is withdrawn from the top of SRC 11 and is decanted to remove 7.7 Kg/Hr water. The hydrocarbon phase from the decanter contains 5.1 Kg/Hr of benzene having 99.99% purity with only trace (<0.01%) of toluene.

This example demonstrates that the total recovery of pure benzene can be achieved by prefractionating the reformate feed and feeding only the $C_7$ and lighter fraction (excluding toluene) to an extractive distillation unit, in which sulfolane/water is used as the solvent.

Example 3

This example demonstrates that a mixture of cyclohexane and benzene from a low conversion, single-bed benzene hydrogenation reactor, can be purified through a back-end extractive distillation column to yield a cyclohexane product with better than 99.9% purity.

Referring to FIG. 1 (or FIG. 2), 100 Kg/Hr of vapor mixture containing 50% benzene and 50% cyclohexane is fed to tray 15 and 200 Kg/Hr of lean solvent containing 99.2% sulfolane and 0.8% water is fed to tray 5 of Extractive Distillation Column 7 consisting of 30 theoretical trays. The S/F is approximately 2.0. EDC 7 is operated at a temperature of 123° C. in the bottom and 70° C. in the top, under a pressure of 1.6 atm in the bottom and 1.1 atm in the top, to recover 49 Kg/Hr overhead stream containing 99.90% cyclohexane and 0.10% benzene after decanting the water from the stream. The recovery per pass of cyclohexane in EDC 7 is 94.7%. The un-recovered cyclohexane is recycled along benzene and the solvent to the front-end Solvent Recovery Column 2.

The energy requirement of the reboiler of EDC 7 is minimized by vaporizing the feed to the column through pressure reduction from the pressure of Hydrogenation Reactor 5 to the pressure of EDC 7. Theoretical stages of EDC 7 can be reduced by increasing S/F, or decreasing the cyclohexane recovery per pass, or both.

Example 4

This example demonstrates that low conversion (40 to 60%) of benzene hydrogenation can be achieved in a single-bed reactor at low reaction temperature without having any diluent in the feed. Only trace of impurities from side reactions are detected in the reactor effluent. Approximately 4 grams of hydrogenation catalyst containing less than 1% platinum supported on alumina was loaded in a down-flow fixed bed reactor. Benzene feed was mixed with hydrogen at a pre-determined ratio in a mixer tube and was fed to the top of the reactor under various reactor conditions. Experimental results from different hydrogenation conditions are presented in Table 4.

TABLE 4

Reactor pressure: 35.0 atm Weight Hourly Space Velocity (WHSV): 4.0 h$^{-1}$

| Temperature (° C.) | $H_2$/Oil (NM$^3$/M$^3$) | Conversion (wt %) | Impurities (wt %) |
|---|---|---|---|
| 120 | 420 | 47.2 | 0.03 |
| 120 | 490 | 58.8 | 0.04 |
| 170 | 420 | 46.5 | 0.05 |
| 170 | 490 | 58.8 | 0.05 |

The data show that, under low hydrogenation temperature (120-170° C.), the conversion was in the range of 47 to 59% in a single-bed reactor. There was essentially no side reaction under these mild conditions, since only trace amounts of impurities were detected in the hydrogenation product (0.03-0.05%). In fact, the conversion at this temperature range was mainly affected by the hydrogen-to-oil ratios.

Example 5

Instead of using the Pt/Al$_2$O$_3$ catalyst of Example 4, a catalyst containing 52% nickel supported on alumina was used. This example also demonstrates that low conversion (40 to 60%) of benzene hydrogenation can be achieved in a single-bed reactor at low reaction temperature without having any diluent in the feed. Again, approximately 4 grams of nickel catalyst was loaded in a down-flow fixed bed reactor. Benzene feed was mixed with hydrogen at a pre-determined ratio in a mixer tube and was fed to the top of the reactor under various reactor conditions. Experimental results from different hydrogenation conditions are presented in Table 5.

TABLE 5

| Reactor pressure: 35.0 atm Weight Hourly Space Velocity (WHSV): 4.0 h$^{-1}$ | | | |
|---|---|---|---|
| Temperature (° C.) | H$_2$/Oil (NM$^3$/M$^3$) | Conversion (wt %) | Impurities (wt %) |
| 200 | 280 | 47.9 | 0.41 |
| 175 | 420 | 61.7 | 0.34 |
| 160 | 420 | 62.3 | 0.16 |

The data show that, under low hydrogenation temperature (160-200° C.), the conversion was in the range of 48 to 62% in a single-bed reactor. Higher impurity content was detected in the liquid reactor effluent with the nickel catalyst as compared to the reactor using the platinum catalyst in Example 4. Depending upon the purity requirement of cyclohexane from the back-end extractive distillation column of this novel process, condition of the hydrogenation reactor can be adjusted accordingly. The back-end extractive distillation column functions to remove benzene, but not the impurities, from the cyclohexane product. The results indicate that higher conversion and lower impurity content (<0.16%) can be achieved by using increased H$_2$/Oil and decreased temperature. Although the nickel catalyst has lower activity than that of the Pt/Al$_2$O$_3$ catalyst, it has much higher tolerance for water and sulfur contents in the feed and therefore is particularly suited for our low conversion applications. Moreover, it is not necessary to use a guard unit when high water and sulfur tolerant nickel catalyst is used in the hydrogenation reactor.

Example 6

This example demonstrates that partial conversion of benzene hydrogenation (with 36 to 56 wt % unconverted benzene in the reactor effluent) can be achieved in a single-bed reactor with a benzene feed containing 26 wt % cyclohexane as a diluent to moderate the reaction rate in order to control the reactor temperature and to minimize the side reactions. Only traces of impurities from side reactions were detected in the reactor effluent. Approximately 4 grams of hydrogenation catalysts containing less than 1% platinum that is supported on alumina was loaded in a down-flow fixed bed reactor. A mixture of benzene and cyclohexane was mixed with hydrogen and fed to the top of the reactor under various reactor conditions. The experimental results are given in Table 6.

TABLE 6

| Reactor pressure: 35.0 atm Weight Hourly Space Velocity (WHSV): 4.0 h$^{-1}$ Feed Composition: 73.7 wt % Benzene and 26.3 wt % Cyclohexane (CH) | | | |
|---|---|---|---|
| Temperature (° C.) | H$_2$/Oil (NM$^3$/M$^3$) | Conversion (wt %) | CH in Product(wt %) |
| 250 | 70 | 23.3 | 43.5 |
| 250 | 140 | 34.1 | 51.4 |
| 250 | 210 | 51.0 | 63.8 |

The data show that, under low hydrogen-to-oil ratios, the conversion of diluted benzene feed was in the range of 23 to 51% at 250° C. in a single-bed reactor. There were essentially no side reactions under these mild conditions. The reactor effluent contained approximately 44 to 64% cyclohexane, which is an ideal feed for the back-end extractive distillation column (EDC 7 in FIG. 1 or EDC 16 in FIG. 2) for producing a high purity cyclohexane product.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A process for removing benzene from a feedstock and recovering cyclohexane that comprises the steps of:
   (a) removing benzene from the feedstock by extractive distillation to yield purified benzene that comprises the steps of:
      (i) introducing the feedstock into a first portion of a first extractive distillation column (EDC) and introducing a first lean extractive distillation (ED) solvent into a second portion of the first EDC which is above the first portion;
      (ii) withdrawing a recovered hydrocarbons stream comprising C$_7$ and lighter non-aromatics from an overhead of the first EDC which is suitable for gasoline blending and collecting a first rich solvent stream C$_6$ and heavier aromatics, C$_8$ and heavier non-aromatics, and solvent from a bottom portion of first EDC;
      (iii) mixing the first rich solvent stream with a second rich solvent that is from a second extractive distillation column (EDC) and feeding the mixture to a first solvent recovery column (SRC) to recover hydrocarbons from an overhead of the first SRC and recycling lean solvent stream from a bottom of the first SRC to both the first EDC and second EDC; and
      (iv) transferring the recovered hydrocarbons stream to an azeotropic distillation column (ADC) to remove benzene/water and cyclohexane/water azeotropes from an overhead of the ADC that is recycled to the first SRC, to recover a benzene and cyclohexane mixture with reduced water levels from a side-cut of the ADC, and to withdraw remaining hydrocarbons from a bottom of the ADC wherein the remaining hydrocarbons are suitable for gasoline blending;
   (b) hydrogenating a portion of the purified benzene in a hydrogenation reactor to yield an effluent that contains a mixture of benzene and cyclohexane; and
   (c) purifying the effluent to produce a product stream containing purified cyclohexane comprises the steps of:
      (i) feeding the effluent containing a mixture of benzene and cyclohexane from the hydrogenation reactor to a first portion of a second extractive distillation column (EDC) and feeding a second lean extractive distillation (ED) solvent to a second portion of the second EDC that is above the first portion;
      (ii) withdrawing purified cyclohexane from an overhead of the second EDC and withdrawing a second rich solvent containing benzene, cyclohexane, and solvent from a bottom of the second EDC; and
      (iii) transferring the second rich solvent to a solvent recovery column (SRC) to recover benzene and cyclohexane from an overhead of the SRC and to recycle lean solvent from a bottom of the SRC to the first EDC and the second EDC.

2. The process of claim 1 wherein the feedstock is reformate.

3. The process of claim 2 wherein the feedstock comprises C$_6$ to C$_{10}$ aromatics and non-aromatics.

4. The process of claim 2 wherein the feedstock comprises at 1 to 10 wt % benzene.

5. The process of claim 2 wherein the feedstock comprises 3 to 6 wt % benzene.

6. The process in claim 1 wherein the first lean ED solvent is selected from the group consisting of sulfolane, a sulfolane with water as co-solvent, a sulfolane and tetraethylene glycol (TTEG) mixture, a sulfolane and TTEG mixture with water as co-solvent, a sulfolane and triethylene glycol (TEG) mixture, a sulfolane and TEG mixture with water as co-solvent, N-formyl morpholine, morpholine, N-methyl-2-pyrrolidone, and 2-pyrrolidone and combinations thereof.

7. The process of claim 1 wherein the first lean ED solvent is sulfolane with water as co-solvent.

8. The process of claim 1 wherein the overhead of the first EDC comprises 1 to 20 wt % of the benzene in the feedstock.

9. The process of claim 1 wherein the overhead of the first EDC comprises 5 to 10 wt % of the benzene in the feedstock.

10. The process of claim 1 wherein the first rich solvent stream from the bottom of the first EDC contains essentially no $C_7$ or lighter non-aromatics.

11. The process of claim 1 wherein the side-cut of the ADC comprises essentially only benzene and cyclohexane with 100 to 1000 ppm water.

12. The process of claim 1 wherein the side-cut of the ADC comprises essentially only benzene and cyclohexane with 100 to 200 ppm water.

13. The process of claim 1 wherein step (b) comprises feeding the benzene and cyclohexane mixture into a hydrogenation reactor to partially hydrogenate the benzene to yield a hydrogenation reactor effluent and transferring the hydrogenation reactor effluent to a phase separator to separate hydrogen gas from liquid components.

14. The process of claim 13 further comprising the step of removing water, sulfur, and nitrogen, if present, from the benzene and cyclohexane mixture before being fed into the hydrogenation reactor.

15. The process of claim 13 wherein water content of the benzene and cyclohexane mixture that is fed into the hydrogenation reactor is in the range of 10 to 100 ppm.

16. The process of claim 13 wherein sulfur content of the benzene and cyclohexane mixture that is fed into the hydrogenation reactor is in the range of 0.5 to 10 ppm.

17. The process of claim 13 wherein the hydrogenation reactor is a one-stage fixed bed or slurry bed reactor.

18. The process of claim 13 wherein the hydrogenation reactor employs a hydrogenation catalyst that comprises platinum catalyst that is supported on alumina or silica.

19. The process of claim 13 wherein the hydrogenation reactor employs a hydrogenation catalyst that comprises a nickel catalyst that is supported on a support that is formed of alumina, titanium oxide, zirconium oxide, or the combination thereof.

20. The process of claim 13 wherein the hydrogenation reactor achieves a benzene hydrogenation conversion to cyclohexane that is controllable to be in the range of 5 to 95% per pass with substantially no side reactions.

21. The process of claim 13 wherein the hydrogenation reactor achieves a benzene hydrogenation conversion to cyclohexane that is controllable to be in the range of 40 to 60% per pass with substantially no side reactions.

22. The process of claim 1 wherein the effluent that is fed to the second EDC is saturated or super saturated vapor that is formed by pressure reduction.

23. The process of claim 1 wherein the second lean ED solvent is sulfolane with water as the co-solvent.

24. The process of claim 1 wherein the level of cyclohexane purity in the purified cyclohexane that is withdrawn from the overhead of the second EDC is regulated by adjusting the degree of cyclohexane recovery in the second EDC.

25. The process of claim 1 wherein the purity of the purified cyclohexane is in the range of 99 to 100 wt %.

26. The process of claim 1 wherein the purity of the purified cyclohexane is in the range of 99.5 to 99.9 wt %.

27. The process of claim 1 wherein the recovery of cyclohexane is in the range of 50 to 95 wt %.

28. The process of claim 1 wherein the first lean ED solvent and the second lean ED solvent are supplied from a common solvent recovery column (SRC).

29. The process of claim 1 wherein, the cyclohexane concentration in the effluent containing the mixture of benzene and cyclohexane that is fed to the second EDC is adjusted to be in the range of 10 to 90 wt % in order to control a two-liquid phase region that develops in the second EDC by-passing a portion of the effluent around the hydrogenation reactor.

30. The process of claim 29 wherein the cyclohexane concentration in the effluent containing the mixture of benzene and cyclohexane that is fed to the second EDC is adjusted to be in the range of 40 to 60 wt % to control the two-liquid phase region in the second EDC.

31. A process for removing benzene from a feedstock and recovering cyclohexane that comprises the steps of:
  (a) introducing the feedstock to a distillation column to recover hydrocarbons containing essentially only benzene and $C_7$ and lighter non-aromatics in an overhead stream of the distillation column and to recover essentially all other components of the feedstock which is suitable for gasoline blending from a bottom of the distillation column;
  (b) removing benzene from the overhead stream of the distillation column in step (a) by extractive distillation to a yield a purified benzene that comprises:
  (i) introducing the overhead stream from the distillation column of step (a) to a first portion of a first extractive distillation column (EDC) and feeding a first lean extractive distillation (ED) solvent to a second portion of the first EDC which is above the first portion;
  (ii) withdrawing the $C_7$ and lighter non-aromatics which are suitable for gasoline blending from an overhead of the first EDC and withdrawing a first rich solvent comprising benzene and solvent from a bottom of first EDC;
  (iii) mixing the first rich solvent from the first EDC with a second rich solvent from a second EDC and feeding the mixture to a first solvent recovery column (SRC) to recover an effluent containing a mixture of benzene and cyclohexane from an overhead of the first SRC and recycling lean solvent from a bottom or the first SRC to both the first EDC and second EDC; and
  (iv) transferring the recovered hydrocarbons to an azeotropic distillation column (ADC) to remove benzene/water and cyclohexane/water azeotropes from an overhead of the ADC for recycling to the first SRC and to recover a benzene and cyclohexane mixture with reduced water from a bottom of the ADC;
  (c) hydrogenating a portion of the purified benzene in a hydrogenation reactor to yield an effluent containing benzene and cyclohexane; and
  (d) purifying the effluent to produce a product stream containing purified cyclohexane comprises the steps of:
  (i) feeding the effluent containing a mixture of benzene and cyclohexane from the hydrogenation reactor to a first portion of a second extractive distillation column (EDC)

and feeding a second lean extractive distillation (F,D) solvent to a second portion of the second EDC that is above the first portion;

(ii) withdrawing purified cyclohexane from an overhead of the second EDC and withdrawing a second rich solvent containing benzene, cyclohexane, and solvent from a bottom of the second EDC; and (iii) transferring the second rich solvent to a solvent recovery column (SRC) to recover benzene and cyclohexane from an overhead of the SRC and to recycle lean solvent from a bottom of the SRC to the first EDC and the second EDC.

32. The process of claim 31 wherein the feedstock is reformate.

33. The process of claim 32 wherein the reformate comprises $C_6$ to $C_{10}$ aromatics and non-aromatics.

34. The process of claim 32 wherein the reformate comprises 1 to 10 wt % benzene.

35. The process of claim 32 wherein the reformate comprises 3 to 6 wt % benzene.

36. The process of claim 31 wherein the overhead stream from the distillation column that is fed to the first EDC comprises 20 to 90 wt % benzene.

37. The process of claim 31 wherein the overhead stream from the distillation column that is fed to the first EDC comprises 30 to 70 wt % benzene.

38. The process of claim 31 wherein the first ED solvent is selected from the group consisting of sulfolane, a sulfolane with water as co-solvent, a sulfolane and tetraethylene glycol (TTEG) mixture, a sulfolane and TTEG mixture with water as co-solvent, a sulfolane and triethylene glycol (TEG) mixture, a sulfolane and TEG mixture with water as co-solvent, N-formyl morpholine, morpholine, N-methyl-2-pyrrolidone, 2-pyrrolidone, and combinations thereof.

39. The process of claim 31 wherein the first ED solvent is sulfolane with water as co-solvent.

40. The process of claim 31 wherein the bottom of the first EDC comprises 80 to 100 wt % of the benzene that is in the overhead stream from the distillation column.

41. The process of claim 31 wherein the bottom of the first EDC comprises 90 to 99 wt % of the benzene that is in the overhead stream from the distillation column.

42. The process of claim 31 wherein the bottom of the first EDC comprises essentially only benzene and solvent.

43. The process of claim 31 wherein the bottom of the ADC comprises essentially only benzene and cyclohexane with 100 to 1000 ppm water.

44. The process in claim 31 wherein the bottom of the ADC comprises only benzene and cyclohexane with 100 to 200 ppm water.

45. The process of claim 31 wherein step (c) comprises feeding the benzene and cyclohexane mixture into a hydrogenation reactor to partially hydrogenate the benzene to yield a hydrogenation reactor effluent and transferring the hydrogenation reactor effluent to a phase separator to separate hydrogen gas from liquid components.

46. The process of claim 45 further comprising the step of removing water, sulfur, and nitrogen, if present, from the purified benzene before being fed into the hydrogenation reactor.

47. The process of claim 45 wherein water content in feed to the hydrogenation reactor is in the range of 10 to 100 ppm.

48. The process of claim 45 wherein sulfur content in the feed to the hydrogenation reactor is in the range of 0.5 to 10 ppm.

49. The process of claim 45 wherein the hydrogenation reactor is a one-stage fixed bed or slurry bed reactor.

50. The process of claim 45 wherein the hydrogenation reactor employs a hydrogenation catalyst that comprises platinum catalyst that is supported on alumina or silica.

51. The process of claim 45 wherein the hydrogenation reactor employs a hydrogenation catalyst that comprises a nickel catalyst that is supported on a support that is formed of alumina, titanium oxide, zirconium oxide, or the combination thereof.

52. The process of claim 45 wherein the hydrogenation reactor achieves a benzene hydrogenation conversion that is controllable to be in the range of 5 to 95% per pass with substantially no side reactions.

53. The process of claim 45 wherein the hydrogenation reactor achieves a benzene hydrogenation conversion that is controllable to be in the range of 40 to 60% per pass with substantially no side reactions.

54. The process of claim 31 wherein the effluent containing a mixture of benzene and cyclohexane that is fed to the second EDC is saturated or super saturated vapor that is formed through pressure reduction.

55. The process of claim 31 wherein the second ED solvent is sulfolane with water as co-solvent.

56. The process of claim 31 wherein the level of cyclohexane purity in the purified cyclohexane that is withdrawn from the overhead of the second EDC is regulated by adjusting the degree of cyclohexane recovery in the second EDC.

57. The process of claim 31 wherein the purity of the purified cyclohexane is in the range of 99 to 100 wt %.

58. The process of claim 31 wherein the purity of purified cyclohexane is in the range of 99.5 to 99.9 wt %.

59. The process of claim 31 wherein the recovery of cyclohexane is in the range of 50 to 95 wt %.

60. The process of claim 31 wherein the first rich solvent and second rich solvent are transferred to the first solvent recovery column (SRC).

61. The process of claim 31 wherein the cyclohexane concentration in the effluent containing the mixture of benzene and cyclohexane that is fed to the second EDC is adjusted to be in the range of 10 to 90 wt % in order to control a two-liquid phase region that develops in the second EDC by-passing a portion of the effluent around the hydrogenation reactor.

62. The process of claim 61 wherein the cyclohexane concentration in the effluent containing the mixture of benzene and cyclohexane that is fed to the second EDC is adjusted to be in the range of 40 to 60 wt % to control the two-liquid phase region in the second EDC.

* * * * *